United States Patent
Novikov et al.

(10) Patent No.: US 10,504,222 B2
(45) Date of Patent: Dec. 10, 2019

(54) SYSTEM, METHOD AND COMPUTER-ACCESSIBLE MEDIUM FOR OBTAINING AND/OR DETERMINING MESOSCOPIC STRUCTURE AND ORIENTATION WITH FIBER TRACKING

(71) Applicants: NEW YORK UNIVERSITY, New York, NY (US); ALBERT-LUDWIGS-UNIVERSITÄT FREIBURG, Freiburg (DE)

(72) Inventors: Dmitry S. Novikov, New York, NY (US); Valerij Kiselev, Freiburg (DE); Marco Reisert, Freiburg (DE)

(73) Assignees: New York University, New York, NY (US); ALBERT-LUDWIGS-UNIVERSITÄT FREIBURG, Freiburg (DE)

( * ) Notice: Subject to any disclaimer, the term of this patent is extended or adjusted under 35 U.S.C. 154(b) by 0 days.

(21) Appl. No.: 14/782,390

(22) PCT Filed: Apr. 7, 2014

(86) PCT No.: PCT/US2014/033189
§ 371 (c)(1),
(2) Date: Oct. 5, 2015

(87) PCT Pub. No.: WO2014/165849
PCT Pub. Date: Oct. 9, 2014

(65) Prior Publication Data
US 2016/0042508 A1    Feb. 11, 2016

Related U.S. Application Data

(60) Provisional application No. 61/808,938, filed on Apr. 5, 2013.

(51) Int. Cl.
A61B 5/00    (2006.01)
G06K 9/46    (2006.01)
(Continued)

(52) U.S. Cl.
CPC .......... G06T 7/0012 (2013.01); A61B 5/0042 (2013.01); A61B 5/055 (2013.01);
(Continued)

(58) Field of Classification Search
None
See application file for complete search history.

(56) References Cited

U.S. PATENT DOCUMENTS

2005/0007100 A1    1/2005    Basser et al.
2006/0229856 A1    10/2006   Burrus et al.
(Continued)

OTHER PUBLICATIONS

Herman, Michael J.. "Simulated Annealing & the Metropolis Algorithm: A Parameter Search Method for Models of Arbitrary Complexity." (2010).*
(Continued)

*Primary Examiner* — Jiangeng Sun
(74) *Attorney, Agent, or Firm* — Hunton Andrews Kurth LLP

(57) ABSTRACT

Exemplary systems, methods, and computer-accessible mediums can be provided that can generate resultant data regarding fiber tract(s) and anatomical structure(s). For example, first information related to imaging data of the anatomical structure(s) can be received. Second information related to a predictive model of further fiber tract(s) can be received. The resultant data can be generated based on the first information, the second information and a fiber cost procedure.

24 Claims, 14 Drawing Sheets

(51) Int. Cl.
| | |
|---|---|
| G06K 9/52 | (2006.01) |
| G06T 7/00 | (2017.01) |
| G06T 7/10 | (2017.01) |
| G06T 7/60 | (2017.01) |
| G06T 7/73 | (2017.01) |
| A61B 5/055 | (2006.01) |
| G01R 33/48 | (2006.01) |
| G01R 33/56 | (2006.01) |
| G01R 33/563 | (2006.01) |

(52) U.S. Cl.
CPC ..... *G01R 33/4806* (2013.01); *G01R 33/5608* (2013.01); *G06K 9/52* (2013.01); *G06T 7/10* (2017.01); *G06T 7/60* (2013.01); *G06T 7/73* (2017.01); *G01R 33/56341* (2013.01); *G06K 2009/4666* (2013.01); *G06T 2207/10088* (2013.01); *G06T 2207/20112* (2013.01); *G06T 2207/30016* (2013.01)

(56) References Cited

U.S. PATENT DOCUMENTS

| | | | | |
|---|---|---|---|---|
| 2007/0124117 | A1* | 5/2007 | Zhang | G01R 33/56341 702/189 |
| 2008/0024131 | A1* | 1/2008 | Wedeen | G01R 33/5617 324/309 |
| 2010/0004527 | A1 | 1/2010 | Dale et al. | |
| 2010/0244834 | A1 | 9/2010 | Mori et al. | |
| 2011/0044524 | A1 | 2/2011 | Wang et al. | |
| 2012/0197105 | A1* | 8/2012 | Mezer | A61B 5/055 600/410 |
| 2012/0280686 | A1* | 11/2012 | White | G01R 33/56341 324/309 |

OTHER PUBLICATIONS

Jennifer Helsby, Monte Carlo Markov Chains: A Brief Introduction and Implementation, 2012. Retrieved from the Internet: <URL: https://web.archive.org/web/20120624005901/http://background.uchicago.edu/~whu/Courses/Ast321_11/Projects/mcmc_helsby.pdf>.*

CS2515, http://www.cs.toronto.edu/~hinton/csc2515/notes/lec6tutorial.pdf , 2007 (Year: 2007).*
International Serach Report for International Application No. PCT/US2014/033189 dated Aug. 28, 2014.
Written Opinion for International Application No. PCT/US2014/033189 dated Aug. 28, 2014.
U.S. Appl. No. 61/560,800, filed Nov. 16, 2011, Fieremans et al.
U.S. Appl. No. 61/163,674, filed Mar. 26, 2009, Novikov et al.
Fillard P, et al. (2011) Quantitative Evaluation of 10 Tractography Algorithms on a Realistic Diffusion MR Phantom. NeuroImage 56 (1): 220-234.
Assaf, Y., et al (2004) New modeling and experimental framework to characterize hindered and restricted water diffusion in brain white matter. Magn. Reson. Med., 52: 965-978.
B Jeurissen et al., (2012) Investigating the Prevalence of Complex Fiber Configurations in White Matter Tissue with Diffusion Magnetic Resonance Imaging, HBM 34: 2747.
SN Jespersen et al., (2007) Modeling dendrite density from magnetic resonance diffusion measurements, NeuroImage 34, 1473.
SN Jespersen et al., (2010) Neurite density from magnetic resonance diffusion measurements at ultrahigh field: Comparison . . . electron microscopy, NeuroImage 49: 205.
E Fieremans et al., (2011) White Matter Characterization with Diffusional Kurtosis Imaging, NeuroImage 58, 177.
S Bells et al., (2011) "Tractometry"—Comprehensive Multi-modal Quantitative Assessment of White Matter Along Specific Tracts, Proc ISMRM 19, 678.
DS Novikov and E Fieremans, (2012) Relating extracellular diffusivity to cell size distribution and packing density . . . white matter, Proc ISMRM 20, 1829.
E Fieremans et al., (2012) Diffusion distinguishes between axonal loss and demyelination in brain white matter, Proc ISMRM 20, 465.
DS Novikov et al., (2014) Revealing mesoscopic structural universality with diffusion, Proc Natl Acad Sci USA, 111, 5088-5093.
DS Novikov et al., (2011) Random walk with barriers Nature, Physics 7, 508.
Reisert, Marco et al., "Global Fiber Reconstruction Becomes Practical," NeuroImage, vol. 54, pp. 955-962, 2011.
Novikov, Dmitry S. et al., "Susceptibility-Induced Increase of Apparent Diffusion Coefficient: BOLD Effect Behind Diffusion fMRI," Proc. Intl. Soc. Mag. Reson. Med., vol. 20, p. 2072, 2012.
Fieremans, E. et al., "In Vivo Measurement of Membrane Permeability and Fiber Size in Calf Muscle Using Time-Dependent DWI," Proc. Intl. Soc. Mag. Reson. Med., vol. 19, p. 1153, 2011.

* cited by examiner

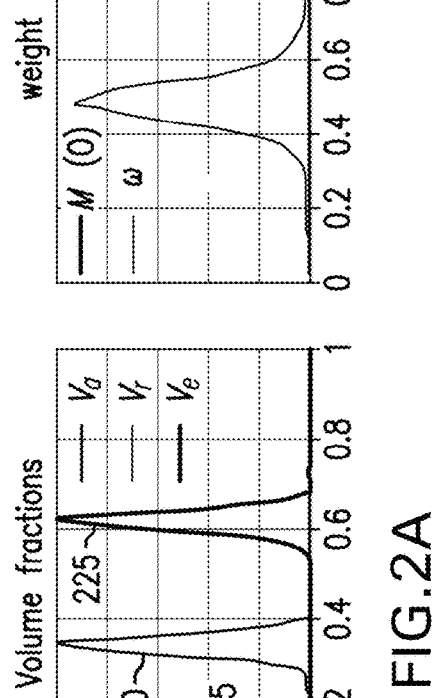
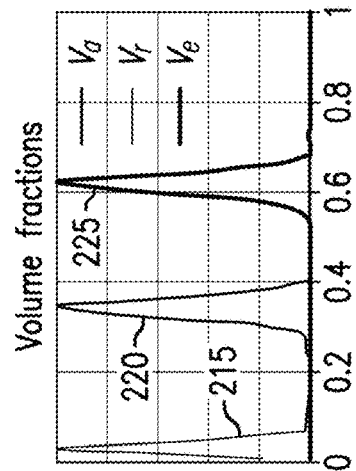
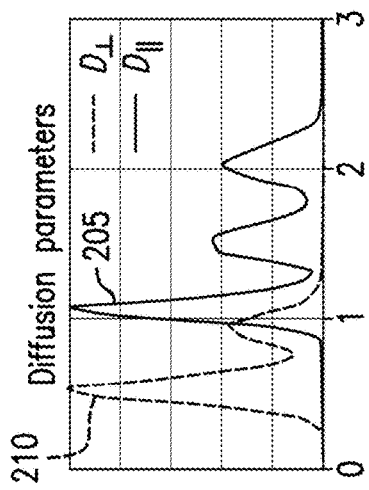
FIG.2A
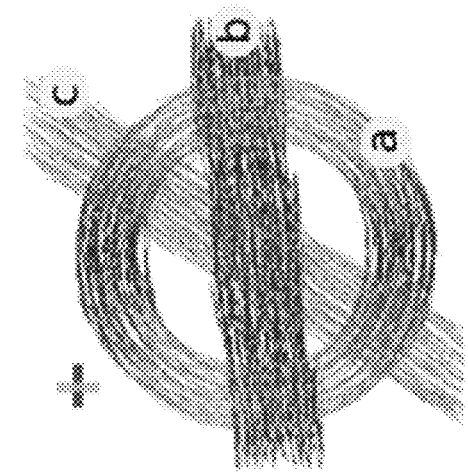
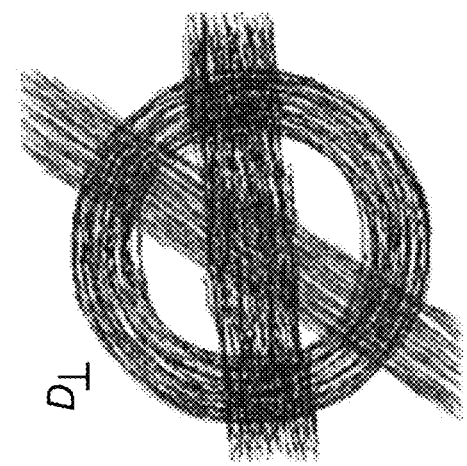
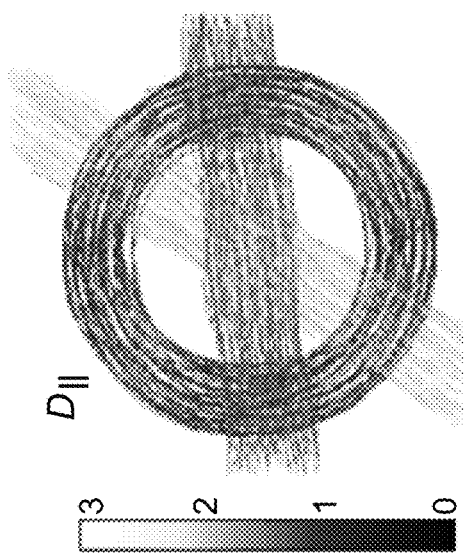
FIG.2B

505

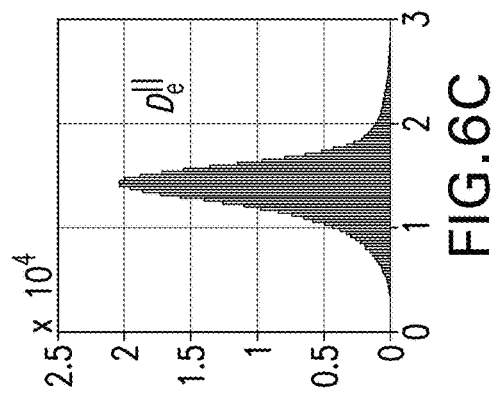
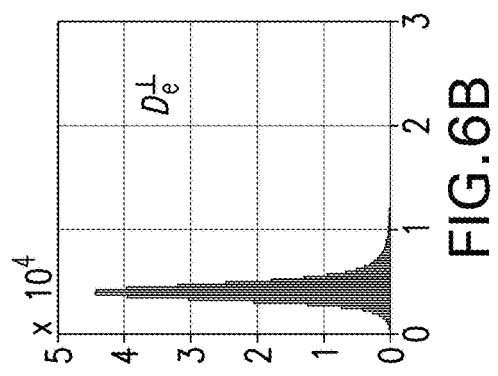
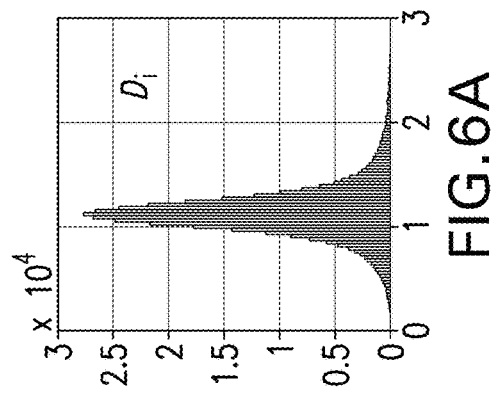
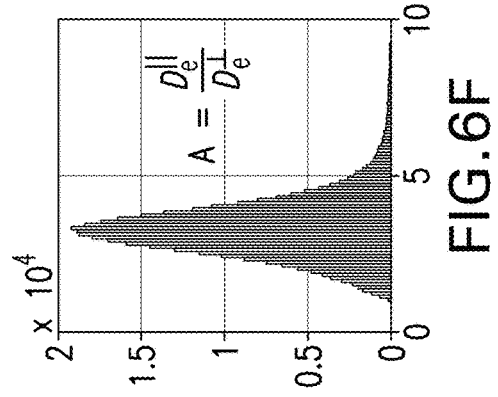
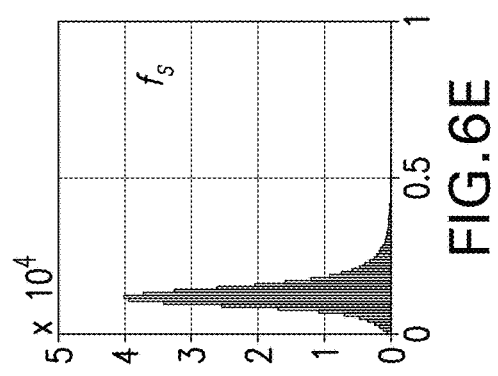
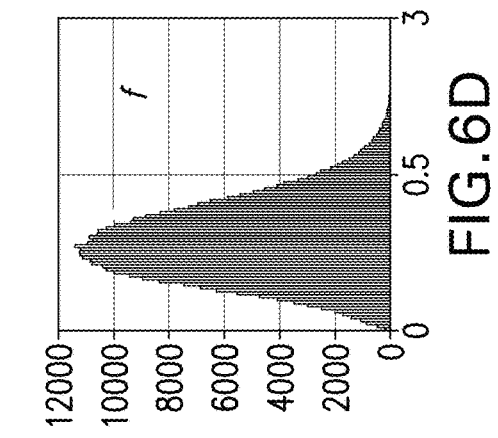

SYSTEM, METHOD AND COMPUTER-ACCESSIBLE MEDIUM FOR OBTAINING AND/OR DETERMINING MESOSCOPIC STRUCTURE AND ORIENTATION WITH FIBER TRACKING

CROSS-REFERENCE TO RELATED APPLICATIONS

This application relates to and claims the benefit and priority from International Patent Application No. PCT/US2014/033189 filed on Apr. 7, 2014, which claims the benefit and priority from U.S. Provisional Patent Application No. 61/808,938, filed on Apr. 5, 2013, the entire disclosures of which are incorporated herein by reference.

FIELD OF THE DISCLOSURE

The present disclosure relates to exemplary systems, methods and computer-accessible mediums for determining, self-consistently, a global geometric organization of neuronal fibers and their local biophysical parameters, based on the measured diffusion-weighted MRI ("dMRI") signal from the brain.

BACKGROUND INFORMATION

Magnetic resonance imaging ("MRI") can produce clinical scans with a spatial resolution of millimeters, however, many disease processes, including Alzheimer's disease, traumatic brain injury and stroke, develop at the cellular level, all at a scale on the order of micrometers, which is about three orders of magnitude below imaging resolution available today.

Therefore, there may be a need to develop a framework with the ability to resolve and quantify nominally invisible (e.g., far below the standard MRI resolution) tissue complexity at the mesoscopic scale. This scale, which can range between a fraction of a μm to tens of μm, can be intermediate ("meso"), between the microscopic scale of molecules (e.g., nanometers), where the nuclear magnetic resonance signal originates, and the macroscopic scale of MRI (e.g., millimeter resolution of clinical MRI scanners). The mesoscopic scale can be the scale of cellular tissue architecture, which can make tissues specific, complex, and radically different from a mere solution of proteins in water.

Currently, there exists a challenge to bridge the meso-macro gap, and to become sensitive to vital changes in structural and functional tissue parameters at the mesoscopic scale. These changes occur, for example, in progressive atrophy of neuronal and glial cells and their processes, loss of myelin sheath, beading, and other specific changes in packing geometry of axons and dendrites and glial cells. This spatial resolution challenge can be fundamental, and overcoming it by the brute-force improvements in hardware alone can yield only incremental advances at an ever-increasing cost. Current clinical MRI systems operate at the physical and physiological bounds on field strength, neuronal stimulation, and energy deposition. These bounds can limit the signal-to-noise ratio, which, combined with bounds on the acquisition time of about 30-60 minutes, can result in a typical imaging voxel size of about a cubic millimeter, far exceeding the desired mesoscopic scale.

A basic principle utilized for probing tissue microarchitecture at the mesoscopic scale can be based on the molecular diffusion, measured with dMRI. Distance covered by diffusing water molecules during typical measurement time, $t$, the diffusion length $L(t)$ approximately 1-30 μm, is generally commensurate with cell dimensions. Therefore, the dMRI measurement can be inherently sensitive to the tissue architecture at the most relevant biological length scales. However, it has been long realized that interpreting dMRI results in terms of the mesoscopic tissue architecture in each imaging voxel can be a very challenging inverse problem. Quantifying mesoscopic tissue parameters within each imaging voxel, and identifying their relative importance, is currently a much discussed, and generally so far an unresolved topic. For example, in one of the recent approaches (See, e.g., References 5, 7 and 8), the mesoscopic structure of brain white matter ("WM") has been quantified in some biologically meaningful terms, but only for those regions in which the neuronal fibers, the constituent units of white matter, can be parallel. This can be a serious limitation for clinical applications, since the presence and crossing of non-parallel fibers can be ubiquitous in the brain (See, e.g., Reference 3). This limitation is especially pronounced in gray matter regions, where the distribution of dendritic and axonal fiber orientations in each imaging voxel can be especially broad (See, e.g., Reference 4).

dMRI technique(s) can provide the possibility to reconstruct, to a certain extent, the geometry of neuronal fibers in brain white matter, which can stretch across many voxels, and connect different brain regions and the brain to the body. A field of multi-voxel connectivity, often referred to as fiber tracking or tractography, has long been complementary to the field of quantifying mesoscopic tissue parameters within each voxel. For the most part, tractography can be based on following the direction of the principal eigenvalue of the diffusion tensor in each voxel, either deterministically or probabilistically. Numerous tractography procedures have been put forth to connect these directions into macroscopic streamlines resembling white matter (e.g., axonal) fibers. Since its introduction in 1999, tractography has become a significant field attracting neuroscientists and computer scientists interested in developing procedures of how to best draw these streamlines. However, certain challenges still remaining for this field are a relative inaccuracy of the resulting streamlines and its lack of robustness with respect to the measurement noise, especially for the less pronounced white matter tracts, and voxels containing multiple fiber directions. Hence, despite its promise, fiber tracking has not yet achieved wide usage for the diagnostics and the pre-surgical planning.

Combining mesoscopic modeling with tractography is not well suited for the conventional fiber tracking procedures, which aim at drawing macroscopic fiber streamlines, since the models and parameters of the mesoscopic tissue architecture (e.g., as the ones outlined above) generally do not have a place in the tracking procedures operating at the scale of voxel dimensions, far exceeding the mesoscopic scale. Therefore, the tractography can use oversimplified models of tissue architecture as a voxel-wise pre-processing step, or, alternatively, tractography results have been utilized merely as a way to segment the tissue and to identify the WM regions, and then, subsequently, to feed these segmentation results to the local voxel-wise models (e.g., the so-called tractometry). (See e.g., Reference 6). In this way, quantifying the mesoscopic tissue structure, and outlining the macroscopic connectivity have remained distinctly separate processing steps.

Thus, it may be beneficial to provide exemplary system, method and computer-accessible medium that can facilitate both the sub-voxel mesoscopic quantification, and the multi-voxel connectivity (e.g., tractography), and which can overcome at least some of the deficiencies described herein above.

SUMMARY OF EXEMPLARY EMBODIMENTS

Exemplary systems, methods, and computer-accessible mediums can be provided that can generate resultant data regarding fiber tract(s) of tissue structure(s). For example, first information related to imaging data of the tissue structure(s) can be received. Second information related to a predictive model of a portion(s) of the fiber tract(s) can be received. The resultant data can be generated based on the first information, the second information and a fiber cost procedure.

In certain exemplary embodiments of the present disclosure, the imaging data can include magnetic resonance imaging data. The magnetic resonance imaging data can comprise further data associated with a diffusion-weighted signal(s). The resultant data can be generated based on an iterative procedure until reaching a predetermined convergence level of both (i) a combination of the first information and the second information, and (ii) the fiber cost function. The predictive model can be based on (i) mesoscopic biophysical model parameters of neuronal tracts of the predictive model, and (ii) geometric model parameters of the neuronal tracts. The geometric parameters can include positions or shapes of the fiber tract(s), and the mesoscopic parameters can vary spatially.

In certain exemplary embodiments of the present disclosure, the neuronal tracts can be represented by a segment(s) of a finite length, and the segment(s) can polymerize to form the fiber tract(s) using a likelihood-maximization procedure. In this exemplary case, the geometric model parameters of the fiber tracts include positions and orientations of all the segments. The fiber cost procedure can be based on at least one of the following: (i) a tendency for neuronal fibers of the predictive model to be locally straight, (ii) a tendency of the neuronal fibers to be continuous, (iii) a tendency for the neuronal fibers to avoid sharp turns, and/or (iv) a tendency for the neuronal fibers to have end portions outside white matter regions of the predictive model. The predictive model can be based on at least one of (i) water fraction of neurites of the predictive model, (ii) water fraction of non-neurite compartments of the predictive model, (iii) diffusion metrics of intra-neurite space of the predictive model, or (iv) diffusion metrics of an extra-neurite space of the predictive model.

In some exemplary embodiments of the present disclosure, the imaging data can be of a region of interest of a portion(s) of the anatomical structure(s), which can be a brain. The likelihood maximization procedure can include a likelihood maximization of all or at least a subset of the parameters. The likelihood maximization procedure can comprise (i) a smooth parameter variation, (ii) a gradual parameter variation, or (iii) a slow parameter variation along the at least one fiber tract, and can include information about a measurement noise, which can be non-Gaussian, and can vary spatially. The predictive model can include local information about a packing geometry of fibers of the predictive model. In some exemplary embodiments of the present disclosure, the predictive model can include local information about (i) a fraction of water, size(s) of building blocks of a nervous tissue and/or (ii) a geometry of the building blocks. In some exemplary embodiments of the present disclosure, the predictive model can include local information about biophysical parameters of myelin sheaths surrounding axons of the predictive model. The predictive model can also include local information about effects of paramagnetic ions on diffusion metrics of the predictive model. In some exemplary embodiments of the present disclosure, the predictive model can be based on axially-symmetric Gaussian diffusion signals. Information related to a prior(s) can be received that can be configured to (a) prevent the predictive model from building non-fiber like tracts, (b) control a number of particles in the fiber tract, and/or (c) control a number of connections in a fiber tract.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features, and advantages of the present disclosure will become apparent from the following detailed description taken in conjunction with the accompanying Figures showing illustrative embodiments of the present disclosure, in which:

FIG. 2A is a set of exemplary histograms of the diffusion parameters, volume fraction, and signal weights, respectively, according to an exemplary embodiment of the present disclosure;

FIG. 2B is a set of exemplary images of exemplary tracking results according to an exemplary embodiment of the present disclosure;

FIGS. 6A-F are exemplary graphs of an exemplary distribution of varying exemplary parameters according to an exemplary embodiment of the present disclosure;

Figure 1:
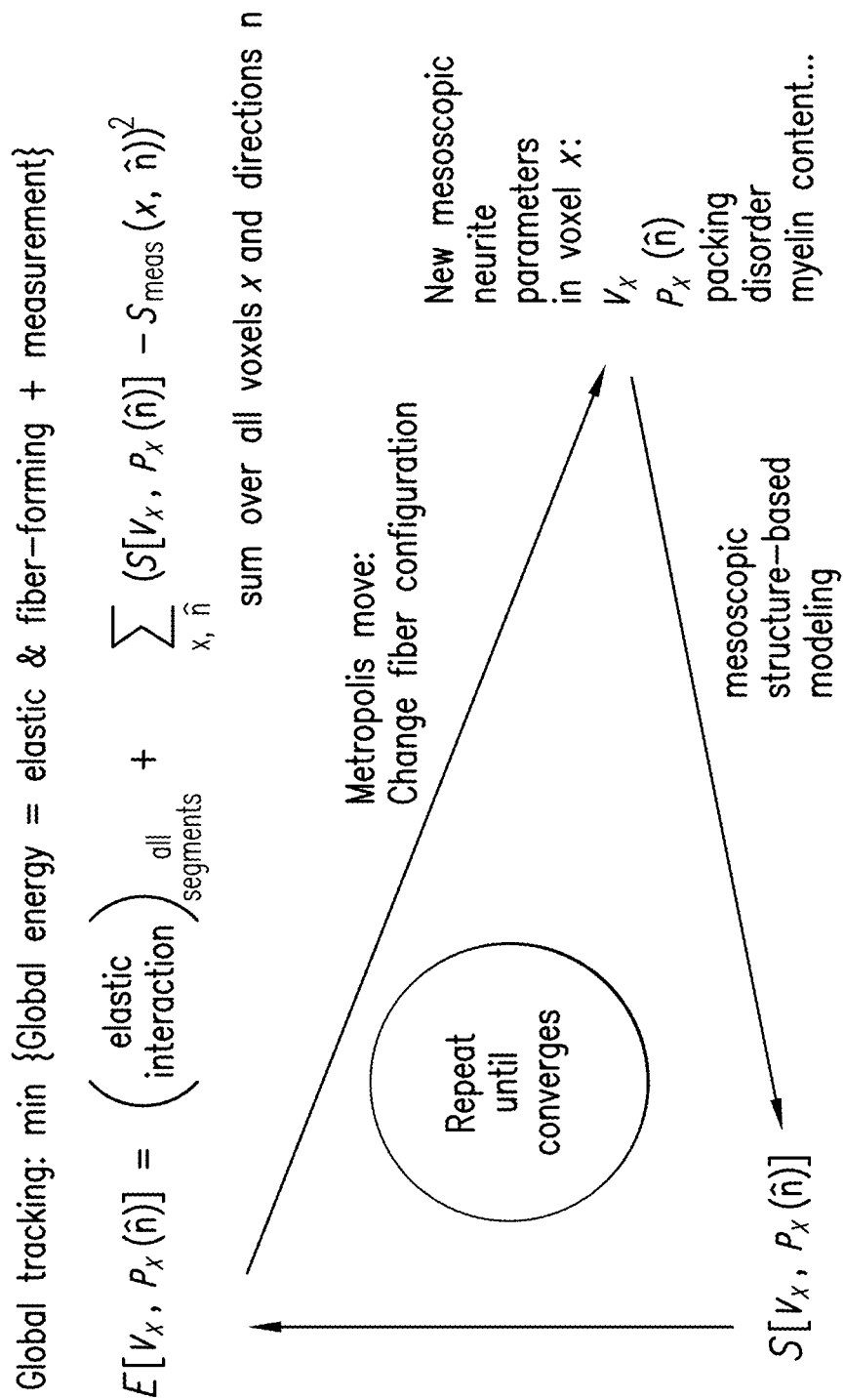
FIG. 1 is an exemplary schematic diagram of the exemplary MesoFT global tracking according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures, or paragraphs provided herein.

DETAILED DESCRIPTION OF EXEMPLARY EMBODIMENTS

According to exemplary embodiments of the present disclosure, it is possible to provide an overarching mesoscale fiber tractography ("MesoFT") framework which can unify quantification of the tissue architecture at the mesoscopic scale with multi-voxel connectivity achieved with global fiber tracking. An iterative and self-consistent nature of the exemplary MesoFT can facilitate the global fiber geometry to affect and optimize the mesoscopic voxel-wise parameters, and vice-versa, the mesoscopic parameters to influence the results of the global fiber tractography.

MesoFT can be the combination of sub-voxel mesoscopic tissue parameters and multi-voxel macroscopic connectivity. The exemplary mesoscopic parameters can be, but not limited to, one or more of the following:

- Volume fraction of water within the neurites, f (See, e.g., Reference 5), can be referred to as "axonal water fraction" in the context of WM fibers.
- Volume fraction of water in the extracellular space.
- Volume fraction of immobilized, or still water, $f_s$.
- Amount and/or fraction of myelin, characterized, for example, by its g-ratio. (See, e.g., References 7, 8, and 11).
- Packing order and/or type for the neuronal fibers and/or glial cells and/or cell bodies.
- Mesoscopic structural parameters such as sizes, distributions of sizes, and packing correlation functions, of the dendrites, axons, beads, synapses and boutons.
- Diffusion coefficient $D_a$ inside the axons (more generally referred to as, for example, neurites). (See, e.g., Reference 5).
- Diffusion coefficients $D_e^{\parallel}$ and $D_e^{\perp}$ parallel and transverse to the neurites in the extra-neurite space. (See, e.g., References 7, 8, and 11).
- Tortuosity of extra-neurite space, which can be defined as $$\Lambda = \frac{D_e^{\parallel}}{D_e^{\perp}}.$$

Given the limitations of a clinical MRI scan, the inverse problem of quantifying the mesoscopic tissue parameters, such as outlined above, in every voxel can be difficult, as there can be many potentially relevant parameters which can determine an outcome of the MRI measurement. To regularize this inverse problem, information about the source of the underlying anisotropy can be utilized, which can include, for example, the fibrous structure of the neurites, (e.g., axons in WM, and both axons and dendrites in gray matter). If one or more dominant directions of the neuronal fibers in each imaging voxel can be available, the determination of the mesoscopic parameters can be much more robust. The exemplary embodiments of system, method, and computer-accessible medium according to the present disclosure can provide a self-consistent determination of both the directions and the mesoscopic parameters, via exemplary combinations of mesoscopic modeling with an exemplary tractography procedure.

The exemplary system, method, and computer-accessible medium, according to exemplary embodiments of the present disclosure, can include and/or utilize the mesoscopic modeling directly into a fiber-tracking scheme. A distinct kind of fiber tracking procedure can be built upon, for example, the global fiber tracking, or Gibbs tracking. (See, e.g., Reference 1).

According to certain exemplary embodiments of the present disclosure, a MesoFT framework can be provided that can unify quantification of the tissue architecture at the mesoscopic scale with multi-voxel connectivity achieved using global fiber tracking. Global tracking can be based on an iterative procedure, which can involve global likelihood maximization (e.g., global energy minimization) over the whole brain for a system of interacting segments that prefer polymerization to form fibers under simulated annealing. (See, e.g., global energy E written below). This procedure can naturally average over uncorrelated noise in different voxels, and therefore can be much more robust (see, e.g., Reference 2). MesoFT can involve modeling the signal S[x, n, $\{f^{(i)}, \ldots \}$] from the collection of segments in each voxel (at position x) in the diffusion direction n. For example, the superscript (i) can label the segment(s) contributing to the signal from a given voxel at position x, and $\{f^{(i)} \ldots \}$ can be the set of mesoscopic parameters (e.g. neurite water fraction f, the immobilized water fraction $f_s$, the diffusion coefficients $D_a$, $D_e^{\parallel}$ and $D_e^{\perp}$ and other parameters) as described below with reference to FIGS. 6A-6F, corresponding to the $i^{th}$ segment. The mesoscopic parameters can further include those inherent to segments and/or an imaging voxel(s). The prediction S[x, n, $\{f^{(i)}, \ldots \}$] can then be iteratively adjusted, by adjusting the segments' mesoscopic $\{f^{(i)}, \ldots \}$ and geometric properties (e.g., positions and orientations), towards the global likelihood maximization, in order to approximate the measured signal $S_{meas}$[x, n], taking into account the fiber cost procedure, as shown in the above equation and in FIG. 1.

To achieve realistic mesoscopic modeling, a predictive biophysical model can be used for each segment (see e.g., References 5, 7, and 8), which can assume that each segment can have parallel neurites with neurite water fraction f, "still" (e.g., immobilized) water fraction $f_s$, diffusion coefficient $D_a$ along them, and zero diffusivity transverse to them. The diffusion in the extra-neurite space can be described by the diffusion coefficients $D_e^{\parallel}$ and $D_e^{\perp}$ along, and transverse to, the segment direction. The positions of neurite segments can be optimized in continuous space, and their contribution to a dMRI signal in a given voxel can be counted in proportion to the fraction of their volume of influence overlapping with the voxel, with the concept of volume of influence outlined in Reference 1. The mesoscopic parameters, such as f, $D_a$, $D_e^{\parallel}$ and $D_e^{\perp}$, can be varied continuously and can be considered "labels" characterizing the mesoscopic properties of each segment. Both the geometric parameters (e.g., positions and orientations of the segments), and the mesoscopic parameters (e.g., f, $D_a$, $D_e^{\parallel}$ and $D_e^{\perp}$) for every segment can be optimized using any procedure having the ability to converge towards a global likelihood maximum (e.g., the Metropolis-Hastings, or simulated-annealing procedure).

The exemplary procedure described herein above can increase the likelihood that the formed macroscopic fibers will be straight, avoiding sharp turns and/or terminations. The exemplary dMRI measurement can add an external "force" acting on the segments to locally line them up along the preferred local direction(s) of the voxel-wise diffusive motion.

The exemplary system, method, and computer-accessible medium, according to an exemplary embodiment of the present disclosure, can utilize the exemplary procedure described herein above by incorporating the prediction(s) of the mesoscopic model(s) into the global optimization procedure. For example, the exemplary system, method, and computer-accessible medium can be based on an iterative procedure, until a predetermined level of convergence can be reached, which can increase the likelihood of, for example:

(i) fiber conformance to prior anatomical knowledge (e.g., fibers having a tendency of being straight and avoiding sharp turns and terminations); and/or (ii) agreement of the predicted and measured signals within each imaging voxel, with the predicted signal calculated as being contributed to and/or from some or all the elementary fiber element(s) (e.g., an elementary segment of a finite length) falling, in part or in full, within a given voxel.

The global likelihood maximization can now be performed with respect to both global fiber geometry (e.g., the numbers, positions and orientations of all the elementary segments), and locally varying mesoscopic parameters of the model(s) that describe the contribution of elementary segments of neuronal tracts to the measured dMRI signal. In such a manner, when the procedure has converged, the physically motivated global fiber directions and connections can be obtained, as well as the voxel-wise mesoscopic parameters (e.g., the parameters described above).

As one illustrative example, the likelihood, obtained over a region of interest or over the whole brain, of the system of interacting elementary fiber segments, can be considered, and can be shown in a flow diagram of FIG. 1. For example, this likelihood, which can be maximized, can be given by exp(−E/T), where E can be the "energy" and T can be "temperature" in the sense of a standard Metropolis-Hastings simulated annealing scheme. Hence, likelihood maximization in this case can be equivalent to finding a global minimum of the energy functional E. The latter can consist of at least two distinct terms, for example:

$$E = (\text{"elastic and fiber-forming interactions"})_{all\ segments} + \Sigma_{x,n} (S[x,n,\{f\_i,\ldots\}] - S_{meas}[x,n])^2$$

The first term can describe an elastic interaction between segments (e.g., the one of the original procedure), as well as the cost of having a given overall number of segments. (See, e.g., Reference 1). This term can make it more preferable for the segments to polymerize into straight fiber sections, avoid sharp turns and terminations within the white matter.

The second term can describe, in the simplest case shown in the equation above, the mean squared deviation between the predicted, $S[x, n, \{f^{(i)}, \ldots\}]$, and the measured, $S_{meas}$, dMRI signal over all participating segments, voxels (x) and diffusion directions (n). A difference between the exemplary system, method and computer-accessible medium and previously known methods can be that the predicted dMRI signal can be based on the adaptive mesoscopic model, which can be suitable for the particular tissue type and whose parameters can be adjusted during the optimization. The contribution from each segment in the predicted signal thus can depend on the relevant mesoscopic parameters, as described above. The overall expression $S[x, n, \{f^{(i)} \ldots\}]$ of the predictive exemplary mesoscopic model in every voxel with coordinates x and for every diffusion direction n can depend on all the geometric parameters (e.g., positions and orientations) and all the mesoscopic parameters (e.g., water fractions $f^{(i)}$, diffusivities, etc.) of the segments entering this voxel, fully or partially. The mesoscopic model(s) specific to different parts of the tissue (e.g. white or gray matter, different brain areas) can enter and affect the outcome of the tractography. Any known mesoscopic tissue model, and any future mesoscopic model, can be used with the exemplary system, method, and computer-accessible medium, thereby affecting the global tractography results, and benefiting from a more robust parametric fit due to having the fiber directions determined self-consistently.

The exemplary system, method, and computer-accessible medium, according to an exemplary embodiment of the present disclosure, can facilitate the contribution of a segment to the predictive exemplary mesoscopic model for diffusion in direction n, which can be, for example:

$$S_{segment}(b,n) = f_s + f_s e^{(-bnDn)} + (1 - f - f_s) e^{-b [D_a(nn\_0)]^2}$$

where b can be the conventional diffusion-weighting parameter (e.g., the b-value). The extra-neurite diffusion tensor D can have eigenvalues $D_a$, $D_e^{\|}$ and $D_e^{\perp}$, and other parameters, which have been introduced above. The contribution of this segment, centered at position $x_0$, can be further multiplied by the exemplary Gaussian "volume of influence" function $v_{x0}(x) = e^{(-(x-x_0)^2/2\sigma^2)}$, where the parameter σ can determine the volume of influence $$v_0 = \pi^{\frac{3}{2}} \sigma^3.$$

The individual segments can then contribute to the overall model prediction $S[x, n, \{f^{(i)}, \ldots\}]$ in each voxel, where the weights can be determined by the overlap of their volumes of influence with the voxel volume.

To further reduce bias in determining geometric and mesoscopic tissue parameters, an exemplary subtraction procedure can be employed. Input data of the exemplary system, method, and computer-accessible medium, which can comprise the diffusion-weighted MRI signal, can have the mean of the data subtract over all diffusion-weighting parameters. This can be done separately for each imaging voxel. Different experimental points can enter the mean with different weights. The exemplary predictive biophysical model can be modified accordingly by subtracting the mean of predicted diffusion-weighted signal computed with the same weights as for the data. At each step of the exemplary iterative procedure of maximizing the likelihood, the subtraction of the mean of predictive biophysical model can be renewed according to the exemplary parameters.

Exemplary Fiber Model

The exemplary fiber model can include, e.g., small segments $X_i \in X$. Each segment can contribute to the predicted MR-signal $M(X_i)$ with a small signal contribution. Each segment can carry its individual diffusion parameters that define this contribution. The segments can connect and polymerize to form long chains (e.g., called fibers). The set of edges connecting the segments can be denoted by E. The complete model F=(X, E, v) can consist of the set of segments, their edges between them and the volume fractions v. The exemplary mesoscopic model M(r, q) can be composed of axially-symmetric Gaussian diffusion signals which can have the form of, for example:

$$m_n^{D_\|, D_\perp}(q) = e^{-D_\|t(q \cdot n)^2 - D_\perp t(|q|^2 - (q \cdot n)^2)} \quad (1)$$

from different white matter compartments, where t can be a fixed diffusion time and the b-value $b=|q|^2 t$). The signal model can be composed of the sum of two such tensor models, where for one of those, the perpendicular diffusion can be zero, and an additional constant reflecting non-diffusing water molecules. So, the signal from the $i^{th}$ segment can be, for example:

$$M_i(r,q) = v_r(r) + m_{n_i}^{D_\|^i, 0}(q) v_a(r) + m_{n_i}^{D_\|^i, D_\perp^i}(q)(1 - v_a(r) - v_r(r)) \quad (2)$$

which is similar to the equation above. Here $v_r$ can be the restricted (e.g., still water) volume fraction $f_s$, $v_a$ can be the axonal (e.g., neurite) water fraction f, and $v_e = 1 - v_a - v_r$ can be the extra-neurite water fraction. The intra-neurite and extra-neurite diffusivities can be equal along the neurite, $D_\|^i = D_e$, $\|^i = D_a^i$.

The total expected signal can be composed of a sum over all segments: $M(r, q) = \lambda_{X_i \in X} w_i I(r, r_i) M_i(q)$, where I can be an indicator function giving contributions if r and $r_i$ can be in same voxel. Each segment can carry 5 or more variables, which can be, for example: $X_i = (r_i, n_i, D_\|^i, D_\perp^i, w_i)$, the position, the direction, the axial diffusivity along the fiber, the perpendicular diffusivity, and its overall weight $w_i$ in the total signal. The volume fractions $f_s(r) = v_r(r)$ of still (non-diffusing) water, axonal water $f(r) = v_a(r)$ and extra-axonal water $v_e(r) = 1 - v_a(r) - v_r(r)$ may not be properties of the segment, but of the position. To increase the number of segments (e.g., to get a higher number of fibers) the voxels can be divided into subvoxels, which can share the same signal.

The cost functional, or energies, can consist of two parts: (a) the data-likelihood and (b) the prior that can regularize the problem and control the connections between the segments. For optimization a simulated annealing approach can be used. The Gibbs distribution $$F = \frac{1}{z} \exp\left(-\frac{(E_{data}(M(X,v)) + E_{prior}(F))}{T}\right)$$

can be simulated while lowering the temperature T. For lower temperature it can be similar to sampling from the minimum of the energy. The simulation principle can be based on a Reversible Jump Monte Carlo Markov Chain ("RJMCMC").

Exemplary Energy: Data Likelihood And Priors

The data term can include a simple quadratic difference between signal and model that can be, approximately assumed to be a Gaussian data likelihood. This assumption can cause a bias on the parameters. However, numerical simulators illustrate that the Rician noise floor can mostly disrupt the $v_r$-fraction leaving the rest of the parameters nearly unbiased.

The priors can control the number of segments, their connections, and can foster smoothness of the variables along fibers. Due to the freedom of the diffusion parameters, a prior can be needed to prevent the fiber model from building unreasonable, non-fiber like configurations. Thus, an additional term $E_{guide}$ can be utilized that can be similar to original data-likelihood, but each segment can have a fixed diffusion model. Very sharp diffusion models, for example, no extra-axonal compartment and high parallel diffusion, can help to resolve sharp crossings. The second prior can control the number of particles, and the third can control the number of connections. To each particle, a cost can be assigned, called chemical potential $E_{chem}(X) = \mu |X|$ where $\mu$ can be strength of the prior, or equivalently the cost of one particle, and |X| can be the total number of particles (segments). Each exemplary segment $X_i$ can have two ports that can make connections with other segments. The exemplary location of the port can be $r \pm \ell n$. If two segments are connected, an additional potential can be turned on which can control, the curvature and the similarity of the diffusion parameters. If the segments X1 and X2 can be connected, then the additional energy can be for example:

$$U_{con}(X_1^{\alpha 1}, X_2^{\alpha 2}) = \lambda_d \sum_{P \in \{D_\|, D_\perp, v\}} (P^1 - P^2)^2 + U_{bend}(X_1^{\alpha 1}, X_2^{\alpha 2})$$

where $\alpha 1$, $\alpha 2$ can specify the ports. The first term can give an additional penalty on differences between the diffusion parameters, for example, it can drive the diffusion parameters to be similar along connected segments.

Exemplary Approximation of Q-Space Correlations

The RJMCMC procedure can be used to compute energy differences like $E_{data}(M + M_{mod}) - E_{data}(M)$. The computation can be dominated by correlations of the current model M with the newly added or modified segment $M_{mod}$, and the correlation of segment $M_{mod}$ with the signal. The spatial part of these correlations can be trivial; however, the q-space part can be quite costly as it can involve the evaluation of the exponential model. To compute or otherwise determine these exemplary correlations efficiently, a power series approximations can be used that can speed up the computation by an order of magnitude. The approximations can be of the following exemplary type:

$$\langle m_n^{D_\|, D_\perp}, S \rangle_Q = \frac{1}{Q} \sum_{k=1}^{Q} m_n^{D_\|, D_\perp}(q_k) S(q_k) \sum_{l,m=1}^{M} \frac{b_{lm}(n)}{(k + D_\|)^l (k + D_\perp)^m}$$

where the $b_{lm}(n)$ can be found by a least squares minimization and the parameter $\kappa$ can be fixed, and can be found empirically to obtain good fits. The form can be similar or based on the Laplace transformation of exponential-type functions. For the two-shell scheme (a: b=1000 and b=2000 shell) considered in the experiments we found $\kappa=4$ to work well. We found values M>6 do not improve fitting accuracy.

Exemplary Procedure

As described herein, the exemplary optimization of the energies can be accomplished by an RJMCMC-type procedure together with a cooling process. The RJMCMC-procedure can be used to repeatedly make random distortions to the current state F. The distortion, called F', can depend on the previous state, and can follow some distribution $P_{prop}(F \to F')$, which can be arbitrarily chosen by the algorithm designer. The only condition can be that the reverse transition has to be possible, for example, $P_{prop}(F' \to F) > 0$. The procedure can have a certain number of initial iterations such that the sequence of generated states can follow the desired distribution and can be in equilibrium. Once equilibrium can be reached, which can be checked by statistics of the energy differences, the system can slowly be cooled down.

Exemplary Segment Generation (e.g., Birth)

A segment $X=(r, n, D_\|, D\bot, w)$ can be provided by selecting most or all parameters uniformly. Then, the energy difference regarding the data-likelihood can be computed or otherwise determined according to $\Delta E_{data} = -2(M_X, S(r))_Q + 2\Sigma_k (M_X, M_k)_Q + (M_X, M_X)_Q$, which can be the sum over k ranges over all segments that lie within the voxel containing the new segment. For the efficient computation of such correlation an exemplary approximation can be used. The computation $\Delta E_{guide}$ can be similar. The Gibbs ratio can be $$R = N_0 \frac{\exp\left(-\frac{(\Delta E_{data} + \Delta E_{guide})}{T}\right)}{(N+1)},$$

where N can be the number of segments currently present and $N_0$ can be the expected number of segments of the underlying Poisson process.

Exemplary Segment Completion (e.g., Death)

A segment X can be randomly chosen. The energy differences that have to be computed can be the negated differences from the birth proposal. The Gibbs ratio can then be R=

$$N \frac{\exp\left(-\frac{(\Delta E_{data} + \Delta E_{guide})}{T}\right)}{(N_0)}.$$

Exemplary Segment Move

A segment X can be randomly selected. The position and orientation can be distorted by normally distributed random numbers, $r' := r + \sigma_s \eta$ and $n' := n + \sigma_n \eta$. The Gibbs ratio can then $$\text{be } R = \exp\left(-\frac{(\Delta E_{data} + \Delta E_{guide} + \Delta E_{con})}{T}\right).$$

A change of segment's diffusion parameter A segment X can be randomly selected. The current diffusion parameters can be distorted by normally distributed random numbers, where the variance can be proportional to the current temperature. The energy difference can then be computed or otherwise determined in for a similar manner to the move above. A change of volume fraction in a random voxel can be chosen. $E_M$ can be called the data energy before the parameter change, then: $E_M = \Sigma_{k,j}(M_k, M_j)_Q - 2\Sigma_k(M_k, S(r))_Q$, where the sum can run over all segments within the voxel. Correspondingly $E_M'$ after the change, then $\Delta E_{data} = E_M' - E_M$. Similar to the diffusion parameters, the new volume fraction can be proposed by distorting the old one by a normal distribution with a variance proportional to the current temperature.

Exemplary Parameters

The segment parameters can be specifically selected. The exemplary length £ can be chosen to be 2 mm, and the potential of connection can be L=0.5. The chemical potential of a segment can be selected proportional to the number Q of measurement in q-space. $\mu=0.005$ Q can be used. That can be, if a segment explains on average more than 0.005 of the variance of the signal, the segment can be maintained. For the strength of $E_{guide}$, $\lambda_{guide}=50T/Tstart$ can be used. For the strength of the connection priors, values of $\lambda_c=1$ and $\lambda_d=1$ can be used. The temperature schedule can start at Tstart=0.3, and can cool down to $T_{end}=0.0025$, which can correspond to a SNR level of $$\frac{1}{\sqrt{Tend}} = 20.$$

The exemplary system, method and computer-accessible medium according to an exemplary embodiment of the present disclosure can utilize the concrete mesoscopic model, wherein each elementary segment can represent a neurite (e.g. axonal) fiber bundle, with the mesoscopic parameters involving axonal water fraction, diffusivity inside and outside axons, and tortuosity of the extra-axonal space. (See, e.g., References 7, 8, and 11). This particular procedure can be implemented and run on real dMRI data obtained in healthy volunteers. Exemplary results can confirm the mutual regularization of biophysical modeling and fiber tracking. It can be possible to obtain mesoscopic biophysical parameters for virtually all fiber tracts in the brain including the crossing regions, which can be a challenge for previously known procedures. These parameters can be tracts specific, which can yield a super resolution of resulted maps, since many neuronal tracts can be present in a given voxel. The regularization effect of modeling on tractography can be expressed in a better quality of resolving the fiber crossings. The exemplary system, method, and computer-accessible medium, according to an exemplary embodiment of the present disclosure, can advance the mesoscopic modeling. Furthermore, by modifying the mesoscopic predictive model, it can also incorporate, as modules, additional features, such as, e.g., effects of paramagnetic ions on the apparent diffusion metrics. (See e.g., References 9 and 10). By modifying the global likelihood function, it can account for non-Gaussian and spatially varying MRI noise.

Exemplary embodiments of the present disclosure of the system, method, and computer-accessible medium can be generalized onto any fibrous tissue, and is not limited to the brain. Indeed, the exemplary system, method and computer-accessible medium can be utilized to, e.g., self-consistently reconstruct the combined geometric and mesoscopic structural parameters; therefore, one straightforward generalization can be to apply the exemplary procedure to, for example, muscle fibers (e.g., skeletal muscle and heart). In such exemplary application, the tendency to form fibers from individual segments can be preserved via the part of the likelihood function similar to the first term in FIG. 1, whereas it can be the exemplary mesoscopic model that can be supplemented, such as described in References 12, 13 and 14.

The system, method and computer-accessible medium according to exemplary embodiments of the present disclosure can be generalized onto and/or utilized for any complex material, and is not limited to biological tissue, and can be further generalized onto any measurement technique, and is not limited to diffusion MRI. The self-consistent determination of the physical parameters of structures below nominal resolution by means of utilizing a predictive physical model incorporated into a self-consistent likelihood maximization procedure, is not limited by the way the measurement can be performed. Therefore, the exemplary system, method, and computer-accessible medium can involve and/or utilize any nondestructive bulk measurement technique (e.g., optical microscopy, super-resolution microscopy, confocal microscopy, rheology, electrical or heat conductivity, etc.).

Exemplary Experiment

The brain in a healthy volunteer can be measured in a 3 T scanner with a diffusion-weighted SE EPI sequence with a resolution 2.2×2.2 mm² in plane and 3 mm in the slice direction with an echo time 165 ms, employing b-factors up to b=8 ms/µm² filling a sphere in q-space in Cartesian manner with total 515 measurement points.

An exemplary 2-shell procedure can be used with b-values of 1000 and 2000 acquired with 60 directions per shell. The in-vivo diffusion measurement was acquired on a Siemens 3T TIM Trio using an SE EPI sequence, with a TE of 107 ms. A healthy male volunteer (e.g., aged 36) was scanned at an isotropic resolution of 2.5 mm. Additionally, a T1 data set was acquired which was segmented into WM, gray matter ("GM"), and cerebral spinal fluid ("CSF") using statistical parametric mapping ("SPM"). White matter was thresholded at a probability of 0.5 to determine the area of reconstruction.

First, a brute force search was performed on a synthetic data. By sweeping through the 3-parameter space of $D_\parallel$, $D_\perp$ and $v_i$, it was determined that the exemplary approximation can accelerate the likelihood computation by a factor of 20 compared to an ordinary implementation. To validate the accuracy of the approximation, a simple crossing/bending configuration (see FIGS. 2A-2E) was simulated including, e.g., three bundles. The central crossing has a crossing angle of 50°. The phantom was simulated on 24×24×9 grid with an isotropic voxel size of 2 mm. Each of the three bundles shown in FIG. 2B has the same axonal volume fraction of 0.4, extra-axonal fraction of 0.6 and different diffusion parameters ($D_\parallel$, $D_\perp$). (See e.g., FIG. 2B). Bundle (a) has (1, 0.5), bundle (b) (1.5, 0.5) and bundle c) (2, 1). Rician noise was added with σ 0.05 corresponding to a SNR of 20. (See, e.g., FIG. 2B).

FIG. 2A shows exemplary histograms of the exemplary tracking results illustrating fitted diffusion parameters, volume fractions, weight parameters, and the tractogram. The reconstructed tracts are shown by directions, by parallel diffusion $D_\parallel$ (element 205) and by perpendicular diffusion $D_\perp$ (element 210). It can be seen that all parameters are nearly unbiased. While the intra axonal water fraction $v_a$ (element 220, having a value of about 0.4) shows a small underestimation, the extraaxonal water fraction $v_e=1-v_a-v_r$ (element 225, having a value of about 0.6) show a small overestimation. The still water fraction (element 215) $v_s$ reflects the Rician noise level of 0.05. M(0) (element 235) shows initial magnetization, which can mimic a normalized water proton density, and w (element 230) shows a weight within a voxel. w (element 23) exhibits a bimodal distribution consistent with having up to two fiber directions (e.g., major fiber directions) within the areas of fiber crossings in the synthetic data, as shown in FIG. 2B.

For the in-vivo dataset, a voxel was subdivided into 3³=27 subvoxels to get a sufficient number of segments/fibers. The running time of the complete tracking procedure took about 10 hours on a Intel 17 (16 GB) with four threads in parallel. The reconstruction contains 1.5 million particles forming about 50000 fibers longer than 10 segments.

Further Exemplary Results

Figure 3A:
FIG. 3A is an exemplary image generated using an exemplary fiber tracking procedure of an entire brain according to an exemplary embodiment of the present disclosure.
Figure 3B:
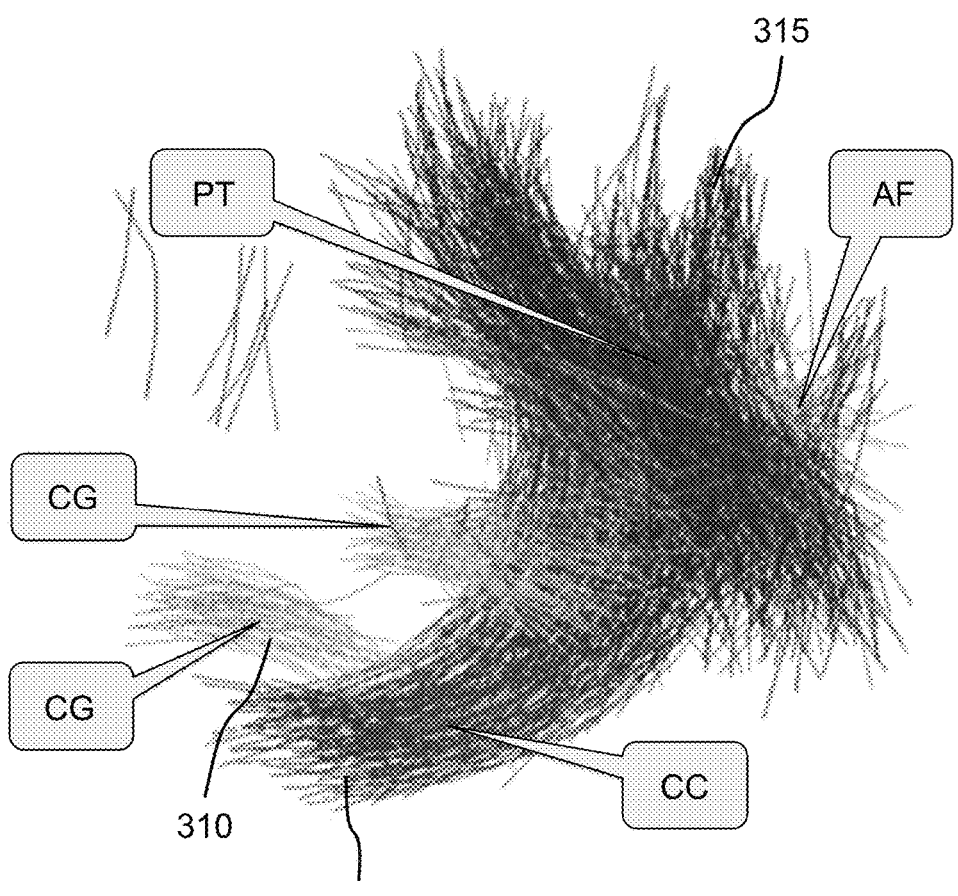
FIG. 3B is an exemplary image of a region of brain white matter which includes a part of corpus callosum generated using an exemplary method, system and computer-accessible medium according to exemplary embodiment of the present disclosure.

FIG. 3A shows an exemplary image of exemplary results of fiber tracking of a whole brain of a volunteer generated using an exemplary method, system, and computer-accessible medium according to an exemplary embodiment of the present disclosure. FIG. 3B shows an exemplary image of a region of the brain white matter (generated using an exemplary method, system, and computer-accessible medium according to an exemplary embodiment of the present disclosure) which can include a part of corpus callosum ("CC") with unidirectional fibers, and an adjacent region with fibers crossing in all three directions. Different fiber orientations can be seen as, for example, 305: right-left, 310: anterior-posterior, and 315: superior-inferior. Further fiber tracts seen in FIG. 3B can be cingulum ("CG"), further association fibers ("AI") and the pyramidal tract ("PT").

Figure 4:
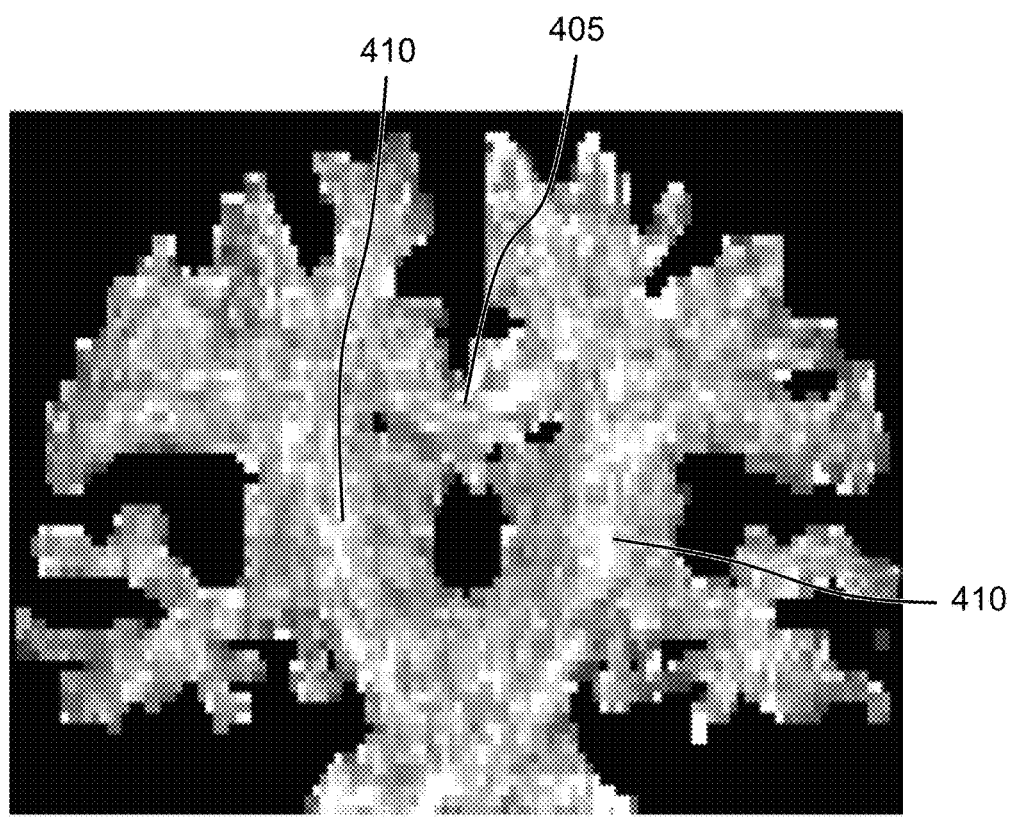
FIG. 4 is an exemplary image of an exemplary graph of a map of the tortuosity of an extra-axonal tensor generated using an exemplary method, system and computer-accessible medium according to an exemplary embodiment of the present disclosure.
Figure 5:
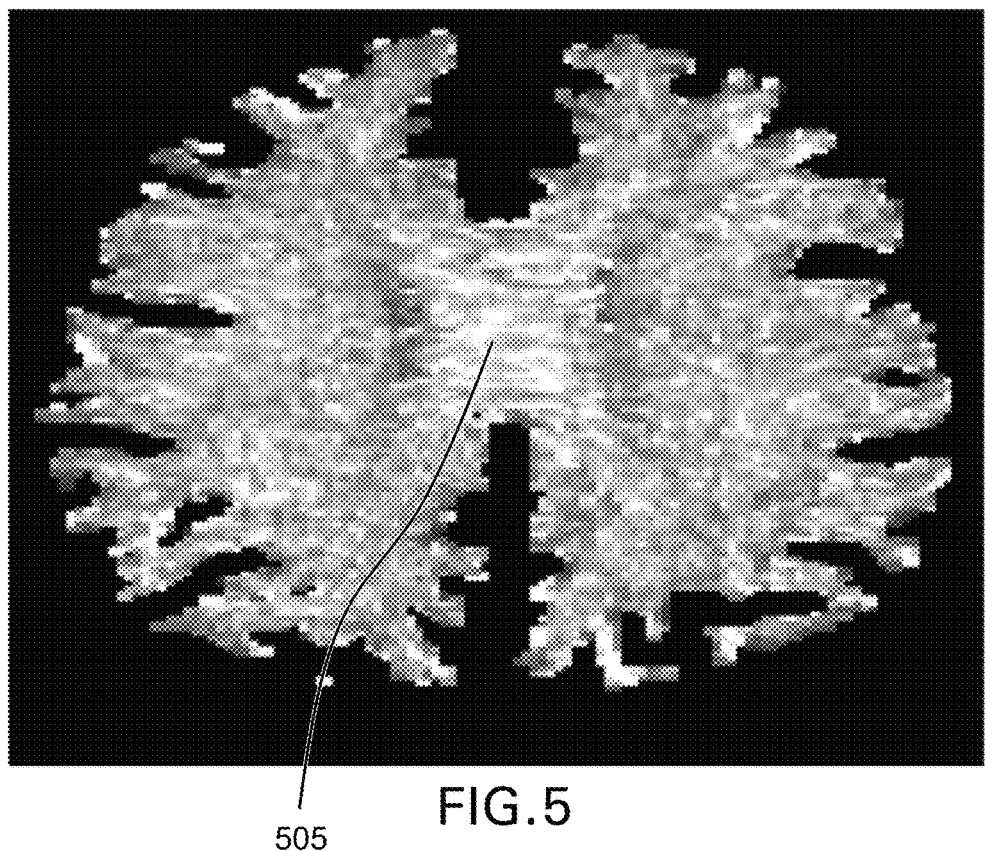
FIG. 5 is a further exemplary image of an exemplary graph of a map of the tortuosity of an extra-axonal tensor generated using an exemplary method, system and computer-accessible medium according to an exemplary embodiment of the present disclosure.
Figure 7:
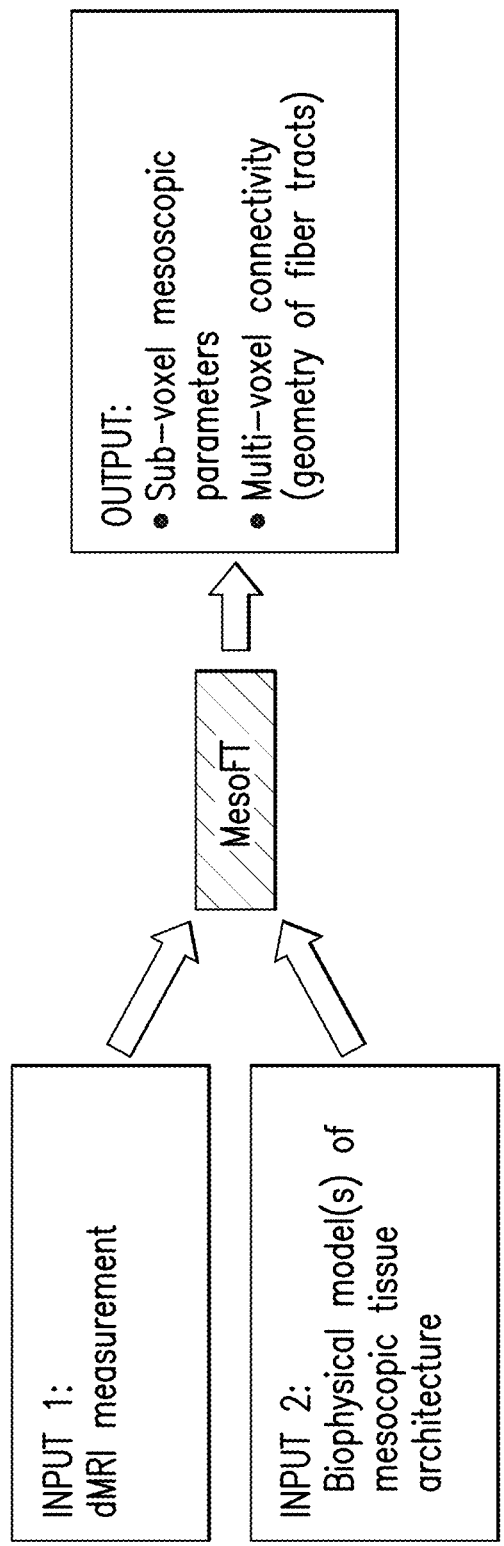
FIG. 7 is a block diagram an exemplary MesoFT procedure according to an exemplary embodiment of the present disclosure.

FIGS. 4 and 5 show exemplary images of exemplary graphs of maps (e.g., coronal and axial sections of the brain, respectively) of the tortuosity of an extra-axonal tensor generated using an exemplary method, system and computer-accessible medium according to an exemplary embodiment of the present disclosure, where $D_e^\parallel$ and $D_e^\perp$ can be the diffusion coefficient in extra-axonal space parallel and orthogonal to the fiber direction, respectively. The tortuosity can be defined as, for example, the ratio $$\Lambda = \frac{D_e^\parallel}{D_e^\perp}.$$

FIGS. 6A-6F show exemplary graphs illustrating exemplary distributions with varying parameters of the exemplary system, method and computer-accessible medium according to an exemplary embodiment of the present disclosure (e.g., Intra-axonal diffusion coefficient Di (FIG. 6A), an extra-axonal diffusion coefficient parallel to fibers $D_e^\parallel$ (FIG. 6C), an extra-axonal diffusion coefficient orthogonal to fibers $D_e^\perp$ (FIG. 6B), an axonal water fraction f (FIG. 6D) and water fraction of immobilized water fs (FIG. 6E)). Additionally an exemplary distribution of the tortuosity $$\Lambda = \frac{D_e^\parallel}{D_e^\perp}$$

of an extra-axonal tensor can be shown in FIG. 6F.

Figure 8A:
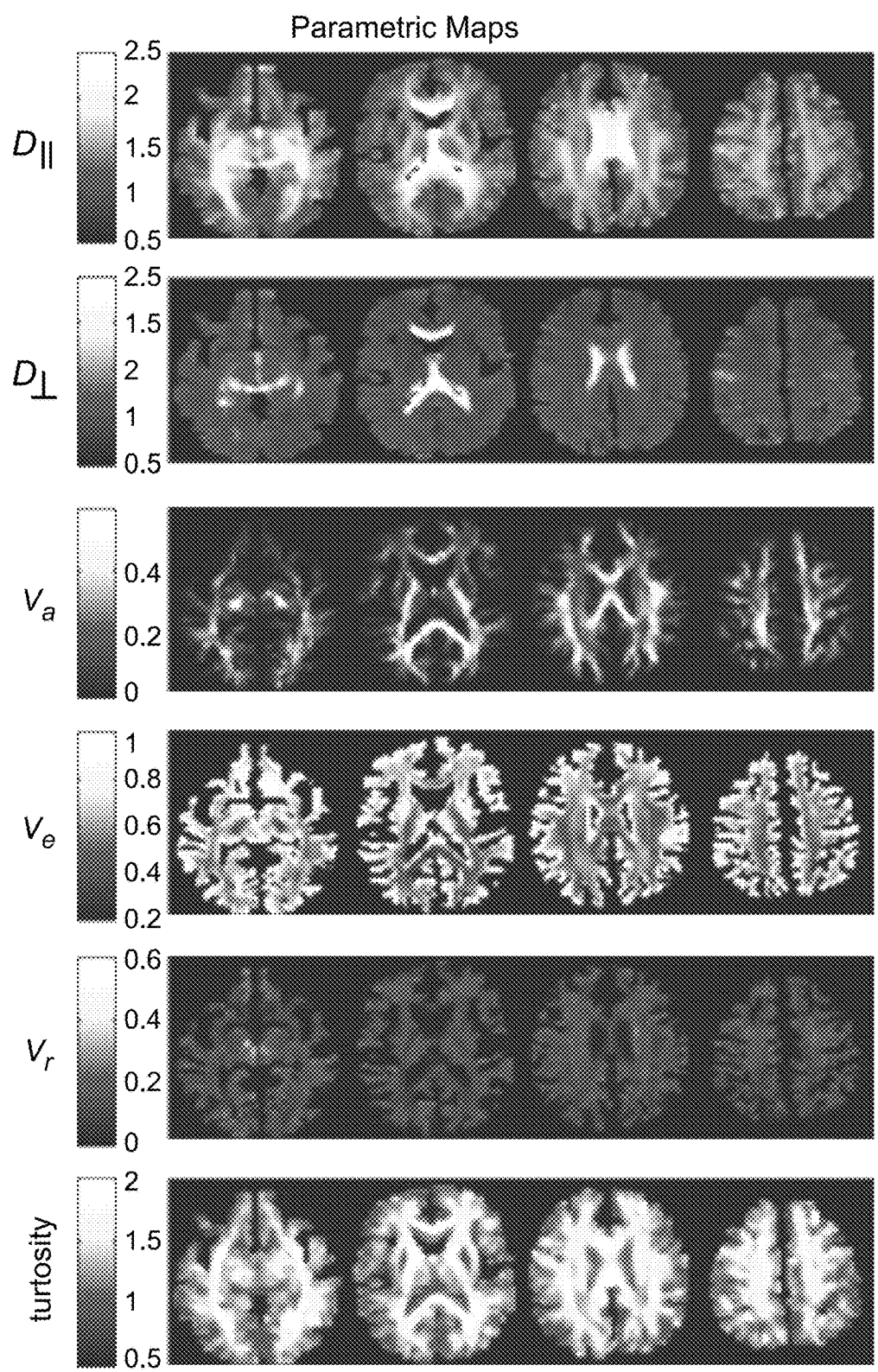
FIGS. 8A-8E are exemplary images of exemplary results of the exemplary fiber model according to an exemplary embodiment of the present disclosure, with FIG. 8B including corresponding exemplary graphs.
Figure 8B:
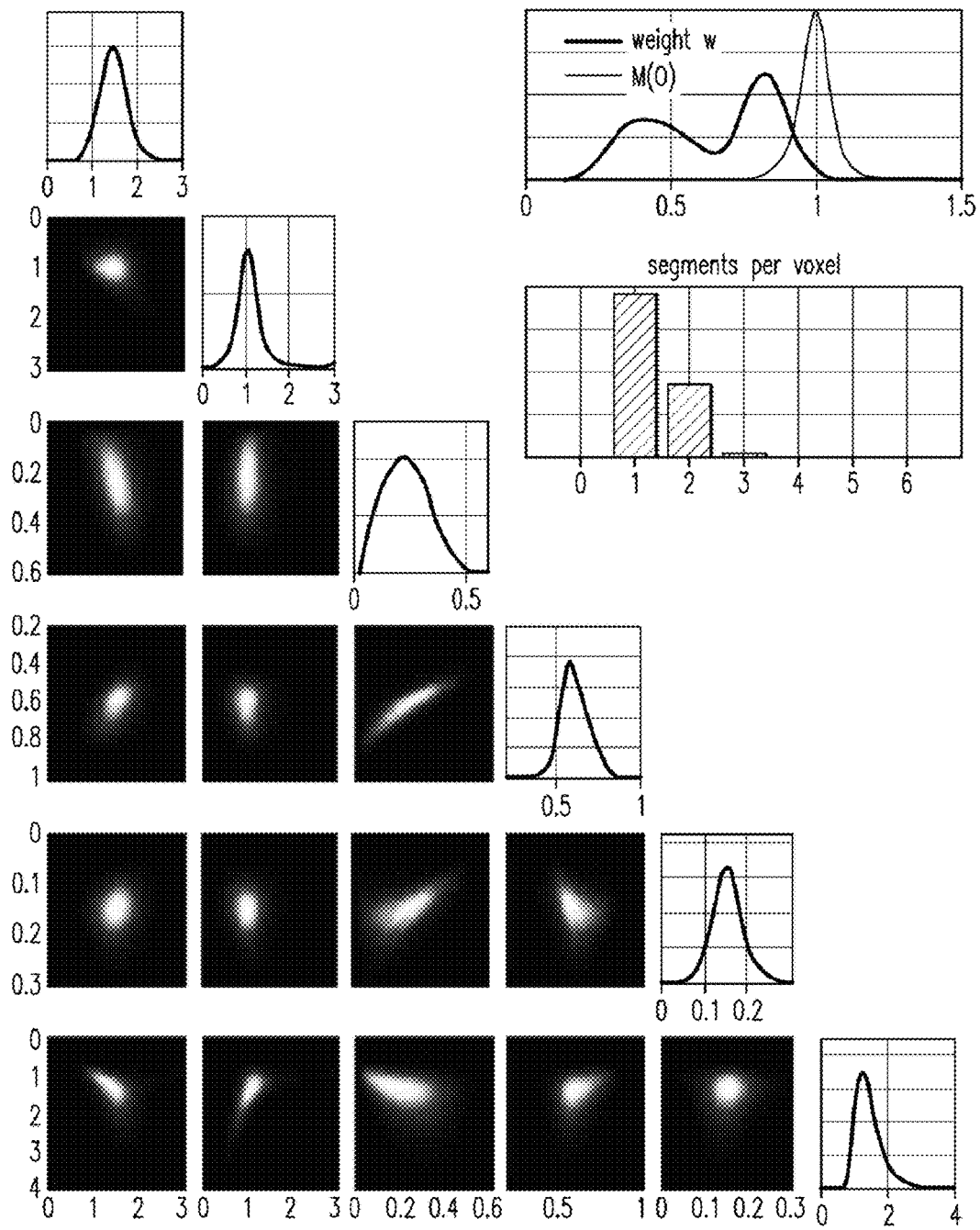
Figure 8C:
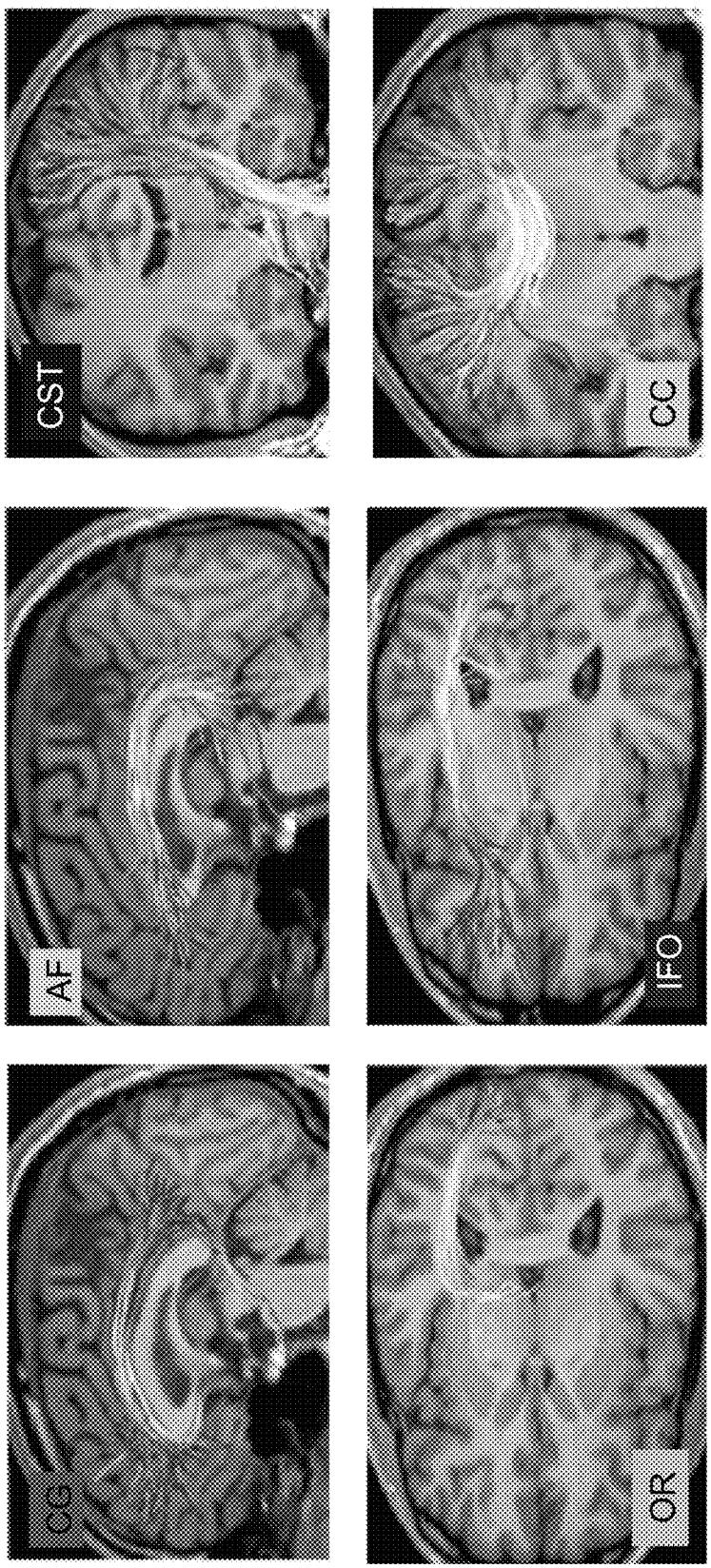
Figure 8E:
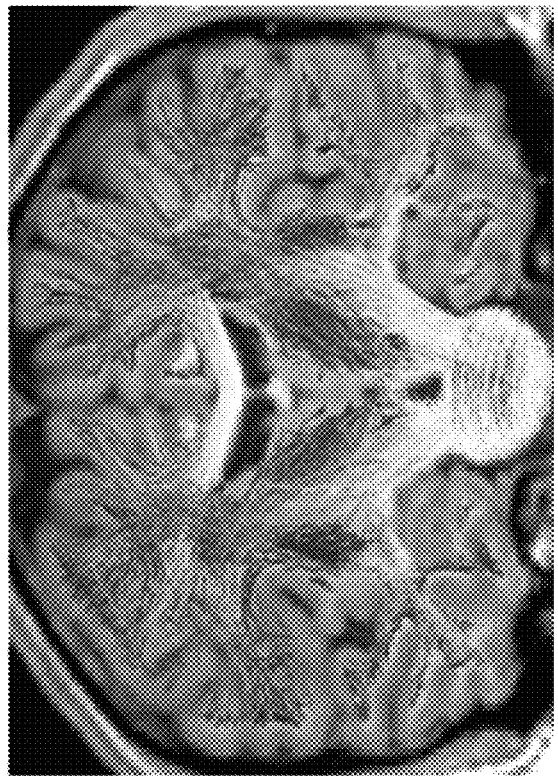
Figure 8D:
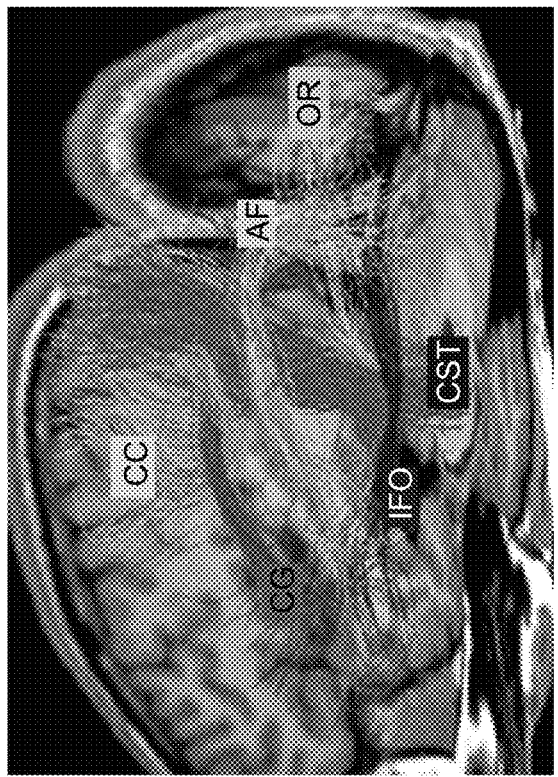

FIGS. 8A-8E illustrate images of exemplary results for the exemplary fiber model above. Exemplary parametric brain maps of the model parameters are shown in FIG. 8A, exemplary first and second statistics of all parameters including tortuosity $$t = \frac{D_\parallel}{D_\perp}$$

shown in FIG. 8B. FIG. 8B also shows graphs of exemplary histograms of the w parameter the can predict a signal at b=0, and the number of segments per voxels. Several tracts were selected in FIGS. 8C and 8D by two ROIs (e.g., Cingulum ("CG"), Arcquate Fascicle ("AF"), Cortical Spinal Tract ("CST"), left Optic Radiation ("OR"), Fronto Occipital Fascicle ("IFO") and callosal fibers to the precentral gyrus ("CC")). FIG. 8E illustrates fibers sliced coronally that were affected by $D_\parallel$.

Exemplary Discussion

The resulting fiber tracts, as shown for the whole brain shown in exemplary images of FIG. 3A and for the region shown in exemplary images of FIG. 3B, can illustrate a variety of local fiber directions and a large number of fiber crossings, in accordance with general anatomical expectations. The exemplary coronal and axial tortuosity maps (see e.g., FIGS. 4 and 5), can correlate well with expected increase in myelin content in the corpus callosum (e.g., 405 of FIG. 4 and center 505 of FIG. 5) and pyramidal tracts (e.g. 410 of FIG. 4). The tortuosity can be another hallmark of the dominance of densely packed WM fibers in large fiber tracts, such as corpus callosum and pyramidal tracts relative to most other WM regions. The exemplary distribution of eigenvalues of extra-neurite diffusion tensor (see e.g., FIG. 6), can, show a notable anisotropy of diffusion in the extra-neurites space. This can be seen in the notable difference between the extra-neurite diffusivities in the parallel and transverse directions, and in the tortuosity values (e.g., their ratio), as also shown in FIGS. 4 and 5, which can indicate that approximating diffusion in the extra-neurite space with an isotropic tensor can generally not be sufficient, and that the above described metrics can be meaningful quantitative characteristics of tissue structure at the mesoscopic scale.

Figure 9:
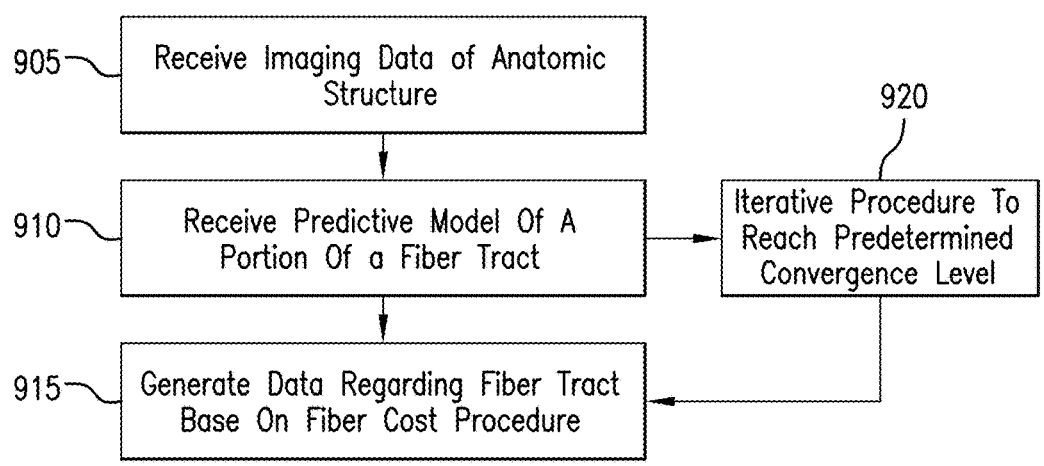
FIG. 9 is an exemplary flow diagram of the exemplary method for generating data regarding a fiber tract according to an exemplary embodiment of the present disclosure.

FIG. 9 shows a flow diagram of an exemplary method for generating data regarding a fiber tract according to an exemplary embodiment of the present disclosure. At procedure 905, imaging data of an anatomical structure to be imaged can be received. For example, at procedure 910, the exemplary predictive model (e.g., the exemplary fiber model), can be applied to the imaging data. At procedure 915, data regarding the fiber tract of the anatomical structure can be generated using an exemplary fiber cost procedure. Alternatively, at step 920, an iterative procedure can be performed until a predetermined convergence level of both (i) a combination of the first information and the second information, and (ii) the fiber cost procedure is achieved, and the data can be generated based on the iterative procedure.

The exemplary system, method, and computer-accessible medium can be viewed as a regularization of sub-voxel modeling via global multi-voxel connectivity. In contrast to using previously known fiber tractography as a guide for comparing other magnetic resonance metrics (See, e.g., Reference 6), the exemplary MesoFT procedure/technique can employ the feedback from the dMRI signal onto delineation of tracts. In general, due to the iterative nature of the exemplary procedure, when the exemplary MesoFT converges, physically motivated fiber directions, connections, voxel-wise neurite densities can be obtained, and, the exemplary system, method and computer-accessible medium can incorporate other mesoscopic parameters such as the degree of myelination (See, e.g., References 7 and 8).

Figure 10:
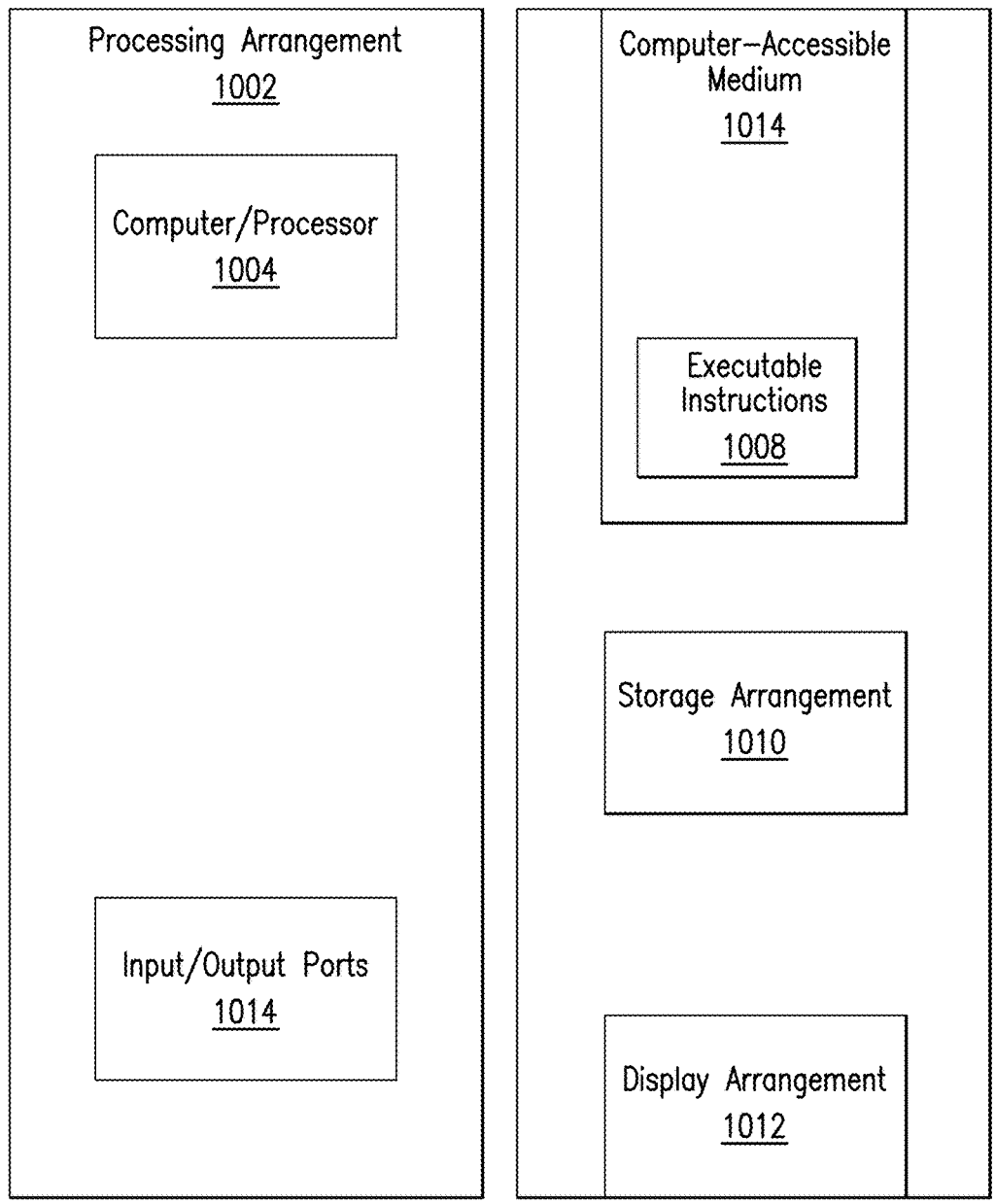
FIG. 10 is an illustration of an exemplary block diagram of an exemplary system in accordance with certain exemplary embodiments of the present disclosure.

FIG. 10 shows a block diagram of an exemplary embodiment of a system according to the present disclosure. For example, exemplary procedures in accordance with the present disclosure described herein can be performed by a processing arrangement and/or a computing arrangement 1002. Such processing/computing arrangement 1002 can be, for example, entirely or a part of, or include, but not limited to, a computer/processor 1004 that can include, for example, one or more microprocessors, and use instructions stored on a computer-accessible medium (e.g., RAM, ROM, hard drive, or other storage device).

As shown in FIG. 10, for example, a computer-accessible medium 1006 (e.g., as described herein above, a storage device such as a hard disk, floppy disk, memory stick, CD-ROM, RAM, ROM, etc., or a collection thereof) can be provided (e.g., in communication with the processing arrangement 1002). The computer-accessible medium 1006 can contain executable instructions 1008 thereon. In addition or alternatively, a storage arrangement 1010 can be provided separately from the computer-accessible medium 1006, which can provide the instructions to the processing arrangement 1002 so as to configure the processing arrangement to execute certain exemplary procedures, processes, and methods, as described herein above, for example.

Further, the exemplary processing arrangement 1002 can be provided with or include an input/output arrangement 1014, which can include, for example, a wired network, a wireless network, the internet, an intranet, a data collection probe, a sensor, etc. As shown in FIG. 10, the exemplary processing arrangement 1002 can be in communication with an exemplary display arrangement 1012, which, according to certain exemplary embodiments of the present disclosure, can be a touch-screen configured for inputting information to the processing arrangement in addition to outputting information from the processing arrangement, for example. Further, the exemplary display 1012 and/or a storage arrangement 1010 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety.

[1] M Reisert et al., NeuroImage 54, 955 (2011).
[2] P Fillard et al., NeuroImage 56, 220 (2011).
[3] Y Assaf et al., Magn Reson Med 52, 965 (2004); B Jeurissen et al., Human Brain Mapping 34, 2747 (2013)
[4] SN Jespersen et al., NeuroImage 34, 1473 (2007); NeuroImage 49, 205 (2010).
[5] E Fieremans et al., NeuroImage 58, 177 (2011).
[6] S Bells et al., Proc ISMRM 19, 678 (2011).
[7] DS Novikov and E Fieremans, Proc ISMRM 20, 1829 (2012).
[8] E Fieremans et al., Proc ISMRM 20, 465 (2012).
[9] DS Novikov et al., Proc Natl Acad Sci USA (2014), doi:10.1073/pnas.1316944111; preprint http://arxiv.org/abs/1210.3014.
[10] DS Novikov et al., Proc ISMRM 20, 2071 (2012).
[11] E Fieremans and DS Novikov, U.S. Provisional Patent Application No. 61/560,800, filed on Nov. 16, 2011, and subsequent full application filed November 2012.
[12] DS Novikov et al., Nature Physics 7, 508 (2011).

[13] DS Novikov et al. System, method and computer-accessible medium for determining membrane properties relating to diffusion, and described in U.S. Patent Application Ser. No. 61/163,674.

[14] E Fieremans et al., *Proc ISMRM* 19, 1153 (2011).

What is claimed is:

1. A non-transitory computer-accessible medium having stored thereon computer-executable instructions for generating resultant data regarding a plurality of fiber tracts of at least one anatomical structure, wherein, when a computer hardware arrangement executes the instructions, the computer arrangement is configured to perform procedures comprising:
   receiving first information related to imaging data of the at least one anatomical structure;
   receiving second information related to a predictive model of at least one further fiber tract that is based on (i) biophysical mesoscopic model parameters of neuronal tracts, and (ii) geometric model parameters of the neuronal tracts, wherein the biophysical mesoscopic model parameters include a diffusion coefficient, and wherein the neuronal tracts comprise a plurality of segments each having a different set of diffusion parameters that are based on the first information; and
   generating the resultant data by simultaneously optimizing the biophysical mesoscopic model parameters and the geometric model parameters based on a fiber cost procedure that is based on (i) a polymerization of the segments into the fiber tracts, and (ii) a distance between a measured magnetic resonance imaging (MRI) signal for the segments and a predicted MRI signal for the segments.

2. The non-transitory computer-accessible medium of claim 1, wherein the imaging data (i) includes MRI data or (ii) is of a region of interest of at least one portion of the at least one anatomical structure.

3. The non-transitory computer-accessible medium of claim 2, wherein the MRI data comprises further data associated with at least one diffusion-weighted signal.

4. The non-transitory computer-accessible medium of claim 1, wherein the computer arrangement is further configured to generate the resultant data based on an iterative procedure until reaching a predetermined convergence level of both (i) a combination of the first information and the second information, and (ii) the fiber cost procedure.

5. The non-transitory computer-accessible medium of claim 1, wherein the geometric model parameters include at least one of at least one position or at least one shape of at least one further segment of the fiber tracts.

6. The non-transitory computer-accessible medium of claim 1, wherein the biophysical mesoscopic parameters vary spatially.

7. The non-transitory computer-accessible medium of claim 1, wherein each of the segments has a finite length.

8. The non-transitory computer-accessible medium of claim 7, wherein the computer arrangement is further configured to polymerize the segments to form the fiber tracts using a likelihood-maximization procedure.

9. The non-transitory computer-accessible medium of claim 1, wherein the fiber cost procedure is further based on at least one of (i) a tendency for neuronal fibers of the predictive model to be straight, (ii) a tendency for the neuronal fibers to avoid sharp turns, (iii) a tendency of the neuronal fibers to be continuous, or (iv) a tendency for the neuronal fibers to have end portions outside white matter regions of the predictive model.

10. The non-transitory computer-accessible medium of claim 1, wherein the predictive model is further based on at least one of (i) water fraction of neurites, (ii) water fraction of non-neurite compartments, or (iii) diffusion metrics of intra-neurite space, (iv) diffusion metrics of an extra-neurite space.

11. The non-transitory computer-accessible medium of claim 1, wherein the at least one anatomical structure is a brain.

12. The non-transitory computer-accessible medium of claim 8, wherein the likelihood maximization procedure includes a global likelihood function of all or at least a subset of the parameters.

13. The non-transitory computer-accessible medium of claim 12, wherein the likelihood maximization procedure comprises at least one of (i) a smooth parameter variation, (ii) a gradual parameter variation, (iii) a slow parameter variation along the fiber tracts or (iv) subtracting a quantity proportional to at least one of a mean or weighted mean of the first information in order to decrease a bias in the resultant data.

14. The non-transitory computer-accessible medium of claim 12, wherein the likelihood maximization procedure includes information about a measurement noise.

15. The non-transitory computer-accessible medium of claim 14, wherein the measurement noise at least one of (i) is non-Gaussian or (ii) varies spatially.

16. The non-transitory computer-accessible medium of claim 1, wherein the predictive model includes local information about at least one of (i) a packing geometry of at least one neurite within an elementary fiber segment, (ii) biophysical parameters of myelin sheaths surrounding axons, or (iii) effects of paramagnetic ions on diffusion metrics.

17. The non-transitory computer-accessible medium of claim 1, wherein the predictive model includes local information about a fraction of at least one of (i) water, (ii) a size of building blocks of a nervous tissue or (ii) a geometry of the building blocks.

18. The non-transitory computer-accessible medium of claim 1, wherein the predictive model is further based on axially-symmetric Gaussian diffusion signals.

19. The non-transitory computer-accessible medium of claim 1, wherein the computer arrangement is further configured to:
   receive information related to at least one prior; and
   at least one of (a) prevent the predictive model from building non-fiber like tracts based on the at least one prior, (b) control a number of particles (segments) in the fiber tracts based on the at least one prior, or (c) control a number of connections in the fiber tracts based on the at least one prior.

20. The non-transitory computer-accessible medium of claim 1, wherein the computer arrangement is configured to optimize the biophysical mesoscopic model parameters and the geometric model parameters using an optimization procedure that converges towards a global likelihood maximum.

21. A system for generating resultant data regarding a plurality of fiber tracts of at least one anatomical structure, comprising:
   a computer hardware arrangement configured to:
      receive first information related to imaging data of the at least one anatomical structure;
      receive second information related to a predictive model of at least one further fiber tract that is based on (i) biophysical mesoscopic model parameters of neuronal tracts, and (ii) geometric model parameters of the neuronal tracts, wherein the biophysical mesoscopic model parameters include a diffusion coefficient, and wherein the neuronal tracts comprise a plurality of segments each having a different set of diffusion parameters that are based on the first information; and generate the resultant data by simultaneously optimizing the biophysical mesoscopic model parameters and the geometric model parameters based on a fiber cost procedure, wherein the fiber cost procedure is based on (i) a polymerization of the segments into the fiber tracts and (ii) a distance between a measured magnetic resonance imaging (MRI) signal for the segments and a predicted MRI signal for the segments.

22. The system of claim 21, wherein the computer hardware arrangement is configured to optimize the biophysical mesoscopic model parameters and the geometric model parameters using an optimization procedure that converges towards a global likelihood maximum.

23. A method for generating resultant data regarding a plurality of fiber tracts of at least one anatomical structure, comprising:

receiving first information related to imaging data of the at least one anatomical structure;

receiving second information related to a predictive model of at least one further fiber tract that is based on (i) biophysical mesoscopic model parameters of neuronal tracts, and (ii) geometric model parameters of the neuronal tracts, wherein the biophysical mesoscopic model parameters include a diffusion coefficient, and wherein the neuronal tracts comprise a plurality of segments each having a different set of diffusion parameters that are based on the first information; and generating the resultant data by simultaneously optimizing the biophysical mesoscopic model parameters and the geometric model parameters based on a fiber cost procedure, wherein the fiber cost procedure is based on (i) a polymerization of the segments into the fiber tracts and (ii) a distance between a measured magnetic resonance imaging (MRI) signal for the segments and a predicted MRI signal for the segments.

24. The method of claim 23, wherein the optimization of the biophysical mesoscopic model parameters and the geometric model parameters is performed using an optimization procedure that converges towards a global likelihood maximum.

* * * * *

UNITED STATES PATENT AND TRADEMARK OFFICE
CERTIFICATE OF CORRECTION

PATENT NO. : 10,504,222 B2
APPLICATION NO. : 14/782390
DATED : December 10, 2019
INVENTOR(S) : Dmitry S. Novikov, Valerij Kiselev and Marco Reisert It is certified that error appears in the above-identified patent and that said Letters Patent is hereby corrected as shown below:

In the Specification

Under Column 1, insert the following paragraph before the "Field of the Disclosure" section:
--STATEMENT REGARDING FEDERALLY SPONSORED RESEARCH
This invention was made with government support under grant number R01 NS088040 awarded by the National Institutes of Health. The government has certain rights in this invention.--

Signed and Sealed this
Seventeenth Day of March, 2020

Andrei Iancu
*Director of the United States Patent and Trademark Office*